US009074513B2

(12) United States Patent
Makki et al.

(10) Patent No.: US 9,074,513 B2
(45) Date of Patent: Jul. 7, 2015

(54) NON-INTRUSIVE EXHAUST GAS SENSOR MONITORING

(75) Inventors: Imad Hassan Makki, Dearborn Heights, MI (US); Pankaj Kumar, Houston, TX (US); James Michael Kerns, Trenton, MI (US); Hassene Jammoussi, Houston, TX (US)

(73) Assignee: Ford Global Technologies, LLC, Dearborn, MI (US)

( * ) Notice: Subject to any disclaimer, the term of this patent is extended or adjusted under 35 U.S.C. 154(b) by 810 days.

(21) Appl. No.: 13/352,885

(22) Filed: Jan. 18, 2012

(65) Prior Publication Data

US 2013/0180509 A1 Jul. 18, 2013

(51) Int. Cl.
*G01N 33/00* (2006.01)
*F01N 11/00* (2006.01)
*F02D 41/14* (2006.01)
*F02D 41/28* (2006.01)

(52) U.S. Cl.
CPC ............ *F01N 11/00* (2013.01); *F02D 41/1474* (2013.01); *F02D 41/1441* (2013.01); *F02D 41/1495* (2013.01); *F02D 2041/1431* (2013.01); *F02D 2041/286* (2013.01)

(58) Field of Classification Search
CPC ......................... F02D 41/1474; F02D 41/1495
USPC .................. 701/107, 109; 123/672, 688, 690, 123/693–697; 73/114.72, 114.73
See application file for complete search history.

(56) References Cited

U.S. PATENT DOCUMENTS

| | | | | | |
|---|---|---|---|---|---|
| 5,065,728 | A | * | 11/1991 | Nakaniwa | 123/683 |
| 5,433,185 | A | * | 7/1995 | Toyoda | 123/682 |
| 5,568,725 | A | * | 10/1996 | Uchikawa | 60/274 |
| 5,685,284 | A | * | 11/1997 | Nakamichi | 123/688 |
| 6,131,446 | A | * | 10/2000 | Schnaibel et al. | 73/114.73 |
| 7,006,909 | B1 | | 2/2006 | May | |
| 7,720,595 | B2 | * | 5/2010 | Iwazaki | 701/114 |
| 7,725,247 | B2 | * | 5/2010 | Iwazaki | 701/114 |
| 7,752,837 | B2 | * | 7/2010 | Iihoshi et al. | 60/277 |
| 2002/0108432 | A1 | * | 8/2002 | Maloney | 73/118.1 |
| 2003/0140680 | A1 | * | 7/2003 | Nagashima et al. | 73/23.32 |
| 2004/0211168 | A1 | * | 10/2004 | Namiki | 60/276 |
| 2005/0161032 | A1 | * | 7/2005 | Nakagawa et al. | 123/673 |
| 2009/0084172 | A1 | * | 4/2009 | Fukagai et al. | 73/114.72 |
| 2009/0112441 | A1 | | 4/2009 | Perschl et al. | |
| 2009/0182490 | A1 | * | 7/2009 | Saunders | 701/114 |
| 2010/0107728 | A1 | * | 5/2010 | Wehmeier et al. | 73/23.31 |
| 2010/0211290 | A1 | * | 8/2010 | Kidokoro et al. | 701/103 |
| 2011/0132341 | A1 | | 6/2011 | Magner et al. | |
| 2011/0314892 | A1 | * | 12/2011 | Wehmeier et al. | 73/1.06 |
| 2012/0080016 | A1 | * | 4/2012 | Bagnasco et al. | 123/673 |

OTHER PUBLICATIONS

Makki, Imad Hassan et al., "Non-Intrusve Exhaust Gas Sensor Monitoring," U.S. Appl. No. 13/352,931, filed Jan. 18, 2012, 29 pages.

* cited by examiner

*Primary Examiner* — Erick Solis
(74) *Attorney, Agent, or Firm* — Julia Voutyras; Alleman Hall McCoy Russell & Tuttle LLP

(57) ABSTRACT

A method for monitoring an exhaust gas sensor coupled in an engine exhaust is provided. In one embodiment, the method comprises indicating exhaust gas sensor degradation based on characteristics of a distribution of extreme values of a plurality of sets of lambda differentials collected during selected operating conditions. In this way, the exhaust gas sensor may be monitored in a non-intrusive manner.

18 Claims, 6 Drawing Sheets

NON-INTRUSIVE EXHAUST GAS SENSOR MONITORING

FIELD

The present disclosure relates to an exhaust gas sensor in a motor vehicle.

BACKGROUND AND SUMMARY

An exhaust gas sensor may be positioned in an exhaust system of a vehicle to detect an air/fuel ratio of exhaust gas exhausted from an internal combustion engine of the vehicle. The exhaust gas sensor readings may be used to control operation of the internal combustion engine to propel the vehicle.

Degradation of an exhaust gas sensor may cause engine control degradation that may result in increased emissions and/or reduced vehicle drivability. Accordingly, accurate determination of exhaust gas sensor degradation may reduce the likelihood of engine control based on readings from a degraded exhaust gas senor. In particular, an exhaust gas sensor may exhibit six discrete types of degradation behavior. The degradation behavior types may be categorized as asymmetric type degradation (e.g., rich-to-lean asymmetric delay, lean-to-rich asymmetric delay, rich-to-lean asymmetric slow response, lean-to-rich asymmetric slow response) that affects only lean-to-rich or rich-to-lean exhaust gas sensor response rates, or symmetric type degradation (e.g., symmetric delay, symmetric slow response) that affects both lean-to-rich and rich-to-lean exhaust gas sensor response rates. The delay type degradation behaviors may be associated with the initial reaction of the exhaust gas sensor to a change in exhaust gas composition and the slow response type degradation behaviors may be associated with a duration after an initial exhaust gas sensor response to transition from a rich-to-lean or lean-to-rich exhaust gas sensor output.

Previous approaches to monitoring exhaust gas sensor degradation, particularly identifying one or more of the six degradation behaviors, have relied on intrusive data collection. That is, an engine may be purposely operated with one or more rich to lean or lean to rich transitions to monitor exhaust gas sensor response. However, these excursions may be restricted to particular operating conditions that do not occur frequently enough to accurately monitor the sensor, such as during deceleration fuel shut off conditions. Further, these excursions may increase engine operation at non-desired air/fuel ratios that result in increased fuel consumption and/or increased emissions.

The inventors herein have recognized the above issues and identified a non-intrusive approach for determining exhaust gas sensor degradation. In one embodiment, a method of monitoring an exhaust gas sensor coupled in an engine exhaust comprises indicating exhaust gas sensor degradation based on characteristics of a distribution of extreme values of a plurality of sets of lambda differentials collected during selected operating conditions.

In this way, exhaust gas sensor degradation may be indicated by monitoring characteristics of a distribution of extreme values from multiple sets of successive lambda samples in steady state operating conditions. In one example, the characteristics may be a mode and central peak of a generalized extreme value (GEV) distribution of the extreme lambda differentials collected during steady state operating conditions. Asymmetric delay or asymmetric slow response degradation may be determined based on the magnitude of the central peak and/or the magnitude of the mode. Further classification, for example symmetric delay or symmetric slow response, may be based on a determined sensor delay or a determined sensor time constant.

By determining degradation of an exhaust gas sensor using a non-intrusive approach with data collected during selected operating conditions, exhaust gas sensor degradation monitoring may be performed in a simple manner. Further, by using the exhaust gas sensor output to determine which of the seven degradation behaviors the sensor exhibits, closed loop feedback control may be improved by tailoring engine control (e.g., fuel injection amount and/or timing) responsive to indication of the particular degradation behavior of the exhaust gas sensor to reduce the impact on vehicle drivability and/or emissions due to exhaust gas sensor degradation.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to an approach for determining degradation of an exhaust gas sensor. More particularly, the systems and methods described below may be implemented to determine exhaust gas sensor degradation based on recognition of any one of six discrete types of behavior associated with exhaust gas sensor degradation.

Figure 1:
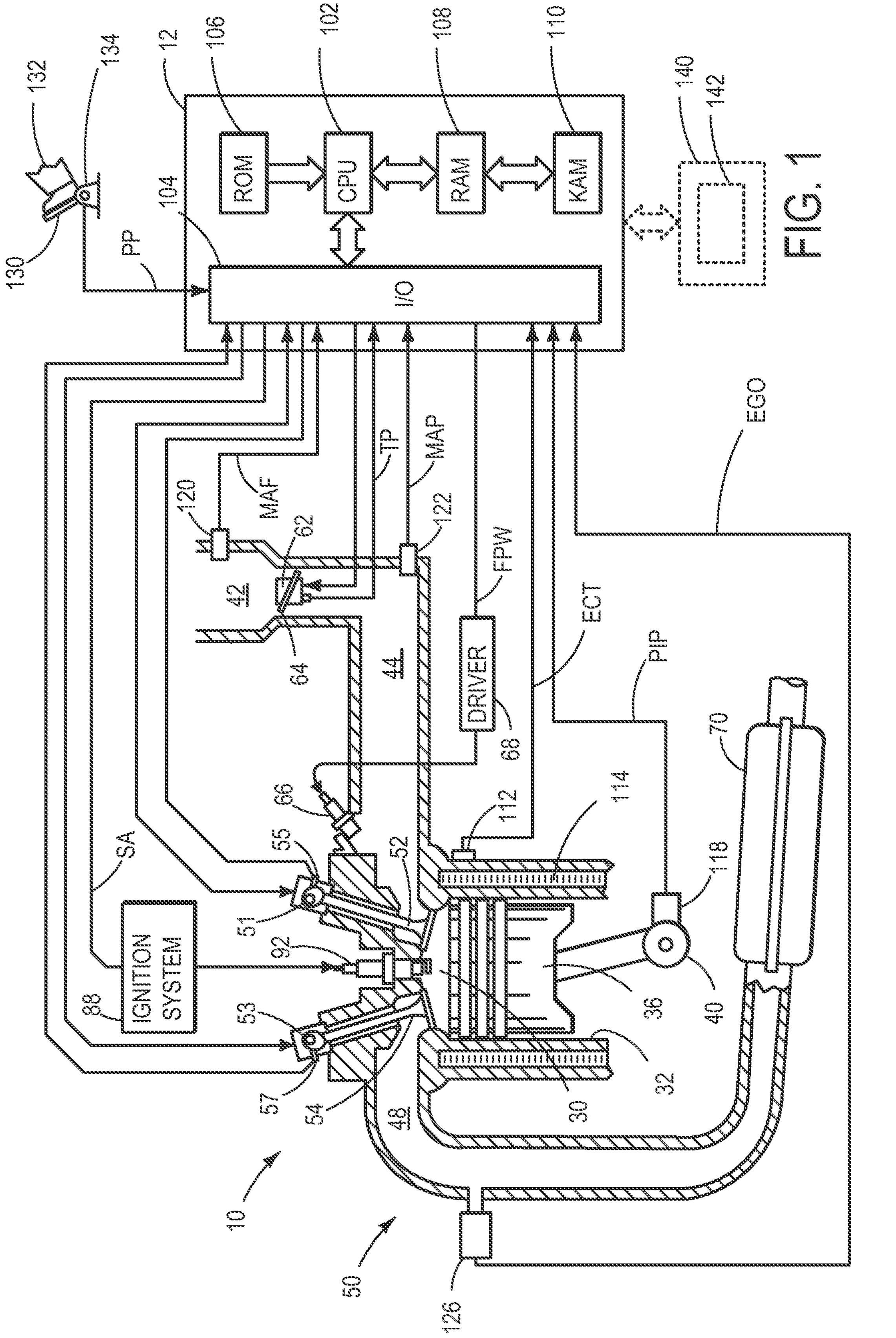
FIG. 1 shows a schematic diagram of an embodiment of a propulsion system of a vehicle including an exhaust gas sensor.

FIG. 1 is a schematic diagram showing one cylinder of multi-cylinder engine 10, which may be included in a propulsion system of a vehicle in which an exhaust gas sensor 126 may be utilized to determine an air fuel ratio of exhaust gas produce by engine 10. The air fuel ratio (along with other operating parameters) may be used for feedback control of engine 10 in various modes of operation. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT) and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

Fuel injector 66 is shown arranged in intake passage 44 in a configuration that provides what is known as port injection of fuel into the intake port upstream of combustion chamber 30. Fuel injector 66 may inject fuel in proportion to the pulse width of signal FPW received from controller 12 via electronic driver 68. Fuel may be delivered to fuel injector 66 by a fuel system (not shown) including a fuel tank, a fuel pump, and a fuel rail. In some embodiments, combustion chamber 30 may alternatively or additionally include a fuel injector coupled directly to combustion chamber 30 for injecting fuel directly therein, in a manner known as direct injection.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 48 of exhaust system 50 upstream of emission control device 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a NOx, HC, or CO sensor. In some embodiments, exhaust gas sensor 126 may be a first one of a plurality of exhaust gas sensors positioned in the exhaust system. For example, additional exhaust gas sensors may be positioned downstream of emission control 70.

Emission control device 70 is shown arranged along exhaust passage 48 downstream of exhaust gas sensor 126. Device 70 may be a three way catalyst (TWC), NOx trap, various other emission control devices, or combinations thereof. In some embodiments, emission control device 70 may be a first one of a plurality of emission control devices positioned in the exhaust system. In some embodiments, during operation of engine 10, emission control device 70 may be periodically reset by operating at least one cylinder of the engine within a particular air/fuel ratio.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP. Manifold pressure signal MAP from a manifold pressure sensor may be used to provide an indication of vacuum, or pressure, in the intake manifold. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses every revolution of the crankshaft.

Furthermore, at least some of the above described signals may used in the exhaust gas sensor degradation determination method described in further detail below. For example, the inverse of the engine speed may be used to determine delays associated with the injection-intake-compression-expansion-exhaust cycle. As another example, the inverse of the velocity (or the inverse of the MAF signal) may be used to determine a delay associated with travel of the exhaust gas from the exhaust valve 54 to exhaust gas sensor 126. The above described examples along with other use of engine sensor signals may be used to determine the time delay between a change in the commanded air fuel ratio and the exhaust gas sensor response rate.

In some embodiments, exhaust gas sensor degradation determination may be performed in a dedicated controller 140. Dedicated controller 140 may include processing resources 142 to handle signal-processing associated with production, calibration, and validation of the degradation determination of exhaust gas sensor 126. In particular, a sample buffer (e.g., generating approximately 100 samples per second per engine bank) utilized to record the response rate of the exhaust gas sensor may be too large for the processing resources of a powertrain control module (PCM) of the vehicle. Accordingly, dedicated controller 140 may be operatively coupled with controller 12 to perform the exhaust gas sensor degradation determination. Note that dedicated controller 140 may receive engine parameter signals from controller 12 and may send engine control signals and degradation determination information among other communications to controller 12.

Note storage medium read-only memory 106 and/or processing resources 142 can be programmed with computer readable data representing instructions executable by processor 102 and/or dedicated controller 140 for performing the methods described below as well as other variants.

As discussed above, exhaust gas sensor degradation may be determined based on any one, or in some examples each, of six discrete behaviors indicated by delays in the response rate of air/fuel ratio readings generated by an exhaust gas sensor during rich-to-lean transitions and/or lean-to-rich transitions. FIGS. 2-7 each show a graph indicating one of the six discrete types of exhaust gas sensor degradation behaviors. The graphs plot air/fuel ratio (lambda) versus time (in seconds). In each graph, the dotted line indicates a commanded lambda signal that may be sent to engine components (e.g., fuel injectors, cylinder valves, throttle, spark plug, etc.) to generate an air/fuel ratio that progresses through a cycle comprising one or more lean-to-rich transitions and one or more rich-to-lean transitions. In each graph, the dashed line indicates an expected lambda response time of an exhaust gas sensor. In each graph, the solid line indicates a degraded lambda signal that would be produced by a degraded exhaust gas sensor in response to the commanded lambda signal. In each of the graphs, the double arrow lines indicate where the given degradation behavior type differs from the expected lambda signal.

Figures 2, 3, 4, 5, 6, 7:
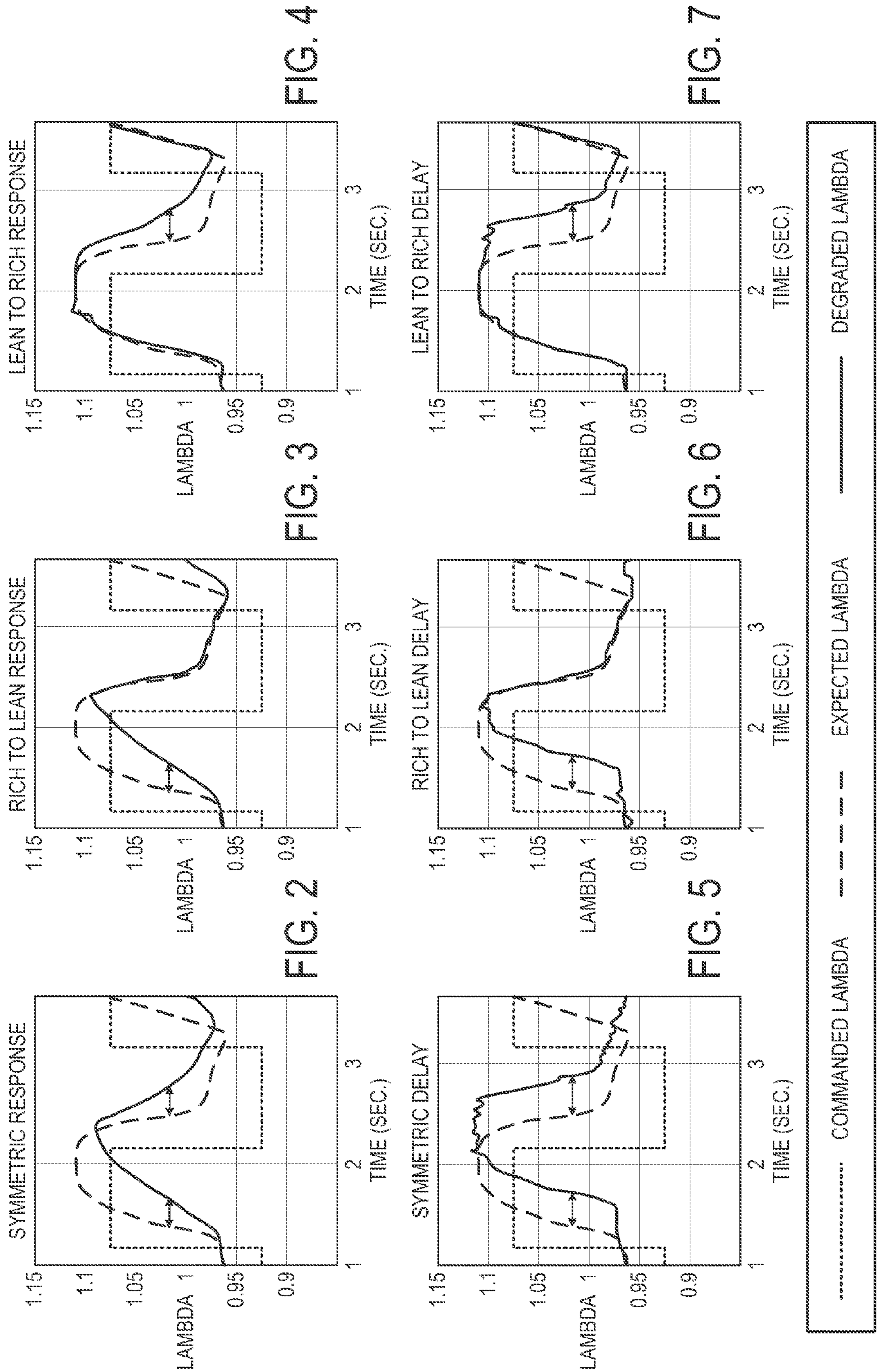
FIG. 2 shows a graph indicating a symmetric response type degradation behavior of an exhaust gas sensor.
FIG. 3 shows a graph indicating an asymmetric rich-to-lean response type degradation behavior of an exhaust gas sensor.
FIG. 4 shows a graph indicating an asymmetric lean-to-rich response type degradation behavior of an exhaust gas sensor.
FIG. 5 show a graph indicating a symmetric delay type degradation behavior of an exhaust gas sensor.
FIG. 6 shows a graph indicating an asymmetric rich-to-lean delay type degradation behavior of an exhaust gas sensor.
FIG. 7 shows a graph indicating an asymmetric lean-to-rich delay type degradation behavior of an exhaust gas sensor.

FIG. 2 shows a graph indicating a first type of degradation behavior that may be exhibited by a degraded exhaust gas sensor. This first type of degradation behavior is a symmetric response type that includes slow exhaust gas sensor response to the commanded lambda signal for both rich-to-lean and lean-to-rich modulation. In other words, the degraded lambda signal may start to transition from rich-to-lean and lean-to-rich at the expected times but the response rate may be lower than the expected response rate, which results in reduced lean and rich peak times.

FIG. 3 shows a graph indicating a second type of degradation behavior that may be exhibited by a degraded exhaust gas sensor. The second type of degradation behavior is an asymmetric rich-to-lean response type that includes slow exhaust gas sensor response to the commanded lambda signal for a transition from rich-to-lean air/fuel ratio. This behavior type may start the transition from rich-to-lean at the expected time but the response rate may be lower than the expected response rate, which may result in a reduced lean peak time. This type of behavior may be considered asymmetric because the response of the exhaust gas sensor is slow (or lower than expected) during the transition from rich-to-lean.

FIG. 4 shows a graph indicating a third type of degradation behavior that may be exhibited by a degraded exhaust gas sensor. The third type of behavior is an asymmetric lean-to-rich response type that includes slow exhaust gas sensor response to the commanded lambda signal for a transition from lean-to-rich air/fuel ratio. This behavior type may start the transition from lean-to-rich at the expected time but the response rate may be lower than the expected response rate, which may result in a reduced rich peak time. This type of behavior may be considered asymmetric because the response of the exhaust gas sensor is only slow (or lower than expected) during the transition from lean-to-rich.

FIG. 5 shows a graph indicating a fourth type of degradation behavior that may be exhibited by a degraded exhaust gas sensor. This fourth type of degradation behavior is a symmetric delay type that includes a delayed response to the commanded lambda signal for both rich-to-lean and lean-to-rich modulation. In other words, the degraded lambda signal may start to transition from rich-to-lean and lean-to-rich at times that are delayed from the expected times, but the respective transition may occur at the expected response rate, which results in shifted lean and rich peak times.

FIG. 6 shows a graph indicating a fifth type of degradation behavior that may be exhibited by a degraded exhaust gas sensor. This fifth type of degradation behavior is an asymmetric rich-to-lean delay type that includes a delayed response to the commanded lambda signal from the rich-to-lean air/fuel ratio. In other words, the degraded lambda signal may start to transition from rich-to-lean at a time that is delayed from the expected time, but the transition may occur at the expected response rate, which results in shifted and/or reduced lean peak times. This type of behavior may be considered asymmetric because the response of the exhaust gas sensor is only delayed from the expected start time during a transition from rich-to-lean.

FIG. 7 shows a graph indicating a sixth type of degradation behavior that may be exhibited by a degraded exhaust gas sensor. This sixth type of behavior is an asymmetric lean-to-rich delay type that includes a delayed response to the commanded lambda signal from the lean-to-rich air/fuel ratio. In other words, the degraded lambda signal may start to transition from lean-to-rich at a time that is delayed from the expected time, but the transition may occur at the expected response rate, which results in shifted and/or reduced rich peak times. This type of behavior may be considered asymmetric because the response of the exhaust gas sensor is only delayed from the expected start time during a transition from lean-to-rich.

It will be appreciated that a degraded exhaust gas sensor may exhibit a combination of two or more of the above described degradation behaviors. For example, a degraded exhaust gas sensor may exhibit an asymmetric rich-to-lean response degradation behavior (i.e., FIG. 3) as well as an asymmetric rich-to-lean delay degradation behavior (i.e., FIG. 6).

Figure 8:
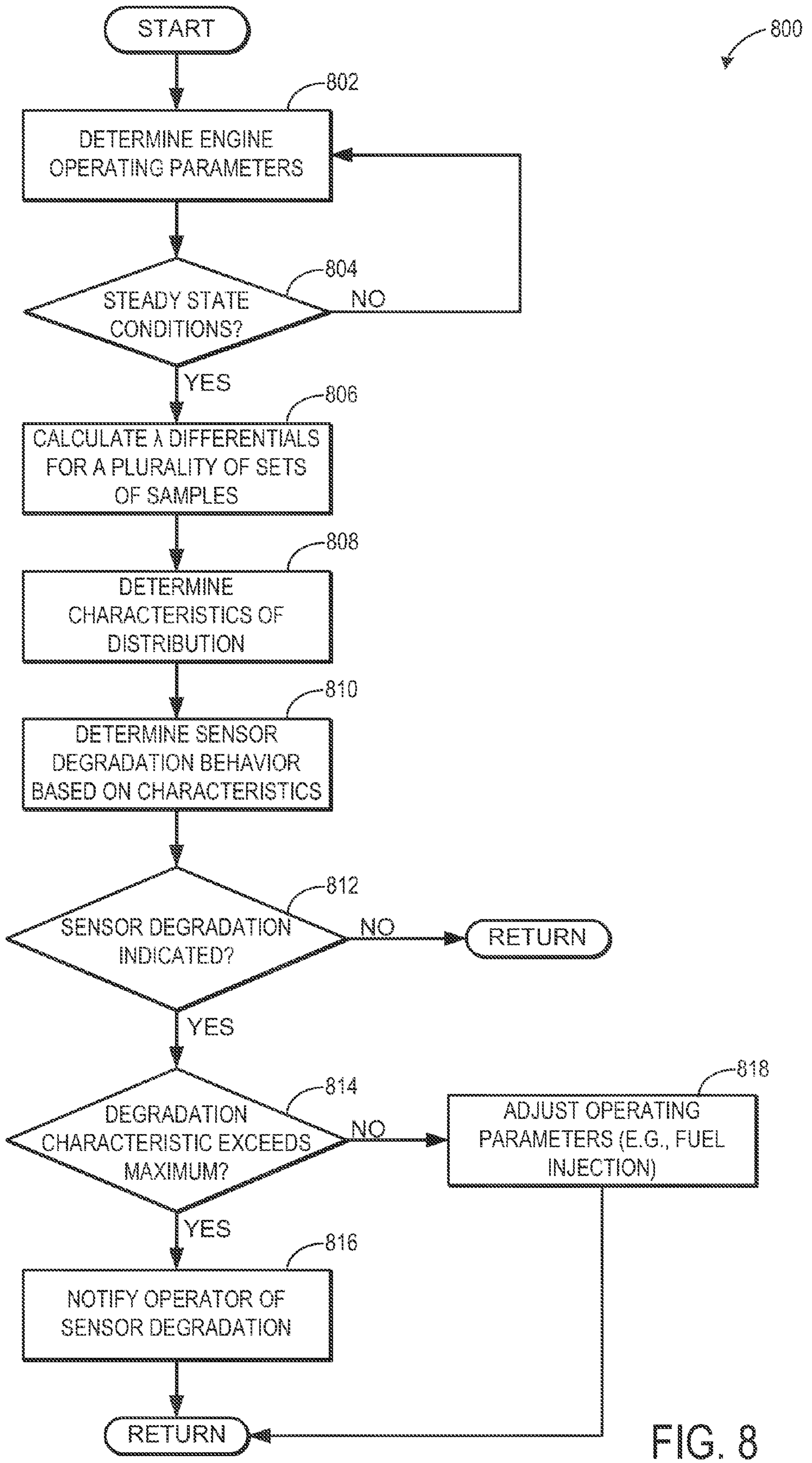
FIGS. 8 and 9 show flow charts illustrating methods for determining exhaust gas sensor degradation behavior according to an embodiment of the present disclosure.
Figure 9:
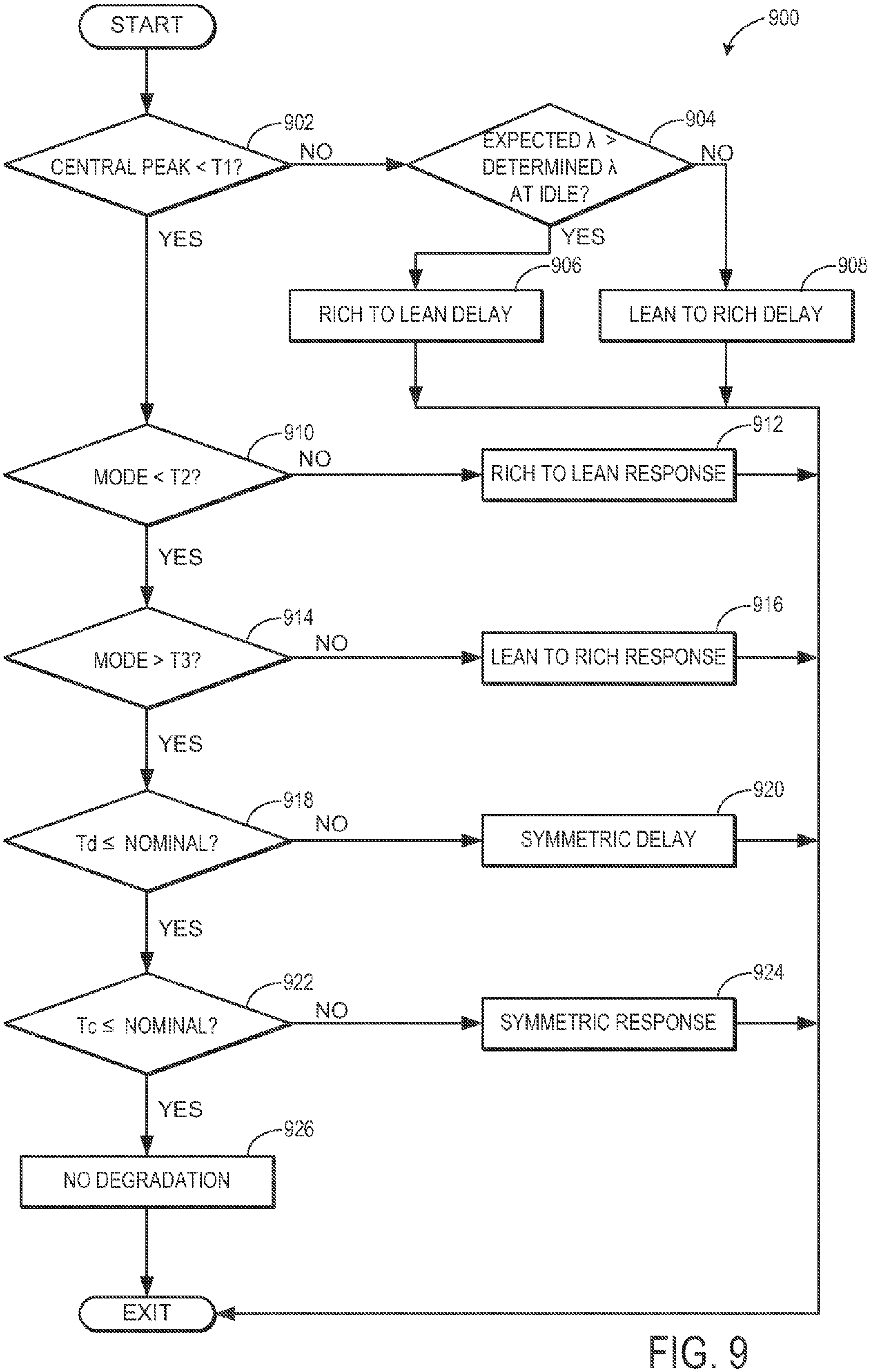

Turning now to FIGS. 8-9, example methods for determining an exhaust gas sensor degradation behavior are depicted according to an embodiment of the present disclosure. FIG. 8 includes a method 800 for monitoring an exhaust gas sensor coupled in an engine exhaust. Method 800 may be carried out by a control system of a vehicle, such as controller 12 and/or dedicated controller 140, to monitor a sensor such as exhaust gas sensor 126. FIG. 9 includes a method 900 that may be carried out as part of FIG. 8 for determining a sensor degradation behavior based on characteristics of a distribution of extreme values of a plurality of data sets. These characteristics, which will be explained in more detail below, are depicted in the example graphs illustrated in FIGS. 11A and 11B.

Referring specifically to FIG. 8, at 802, method 800 includes determining engine operating parameters. Engine operating parameters may be determined based on feedback from various engine sensors, and may include engine speed, load, air/fuel ratio, temperature, etc. Further, engine operating parameters may be determined over a given duration, e.g., 10 seconds, in order to determine whether certain engine operating conditions are changing, or whether the engine is operating under steady-state conditions. As such, method 800 includes, at 804, determining if the engine is operating in steady-state conditions based on the determined engine operating parameters. Steady-state conditions may be determined based on certain operating parameters changing less than a threshold amount during the given duration. In one example, steady-state conditions may be indicated if the engine is operating at idle, or if engine speed varies by less than 20%, engine load varies by less than 30%, and engine air/fuel ratio varies by less than 0.15. In some embodiments, steady-state conditions may also include engine temperature varying by less than a threshold amount, or engine temperature being above a threshold amount. This may avoid monitoring the sensor during cold engine operation, when the sensor may not be heated and thus may not be producing accurate output.

If it is determined at 804 that the engine is not operating in steady-state conditions, method 800 returns to 802 to continue to determine engine operating parameters. If steady state conditions are determined, method 800 proceeds to 806 to calculate air/fuel ratio, or lambda, differentials for a given duration based on readings from the exhaust gas sensor being monitored (e.g., sensor 126). Lambda may be determined for a given number of samples over a given time duration, for example samples may be collected at a rate of 1 sample/96 ms for 60 seconds. For each sample, the difference between that determined lambda and the previous lambda may be calculated and stored in the memory of the controller.

The lambda differentials are plotted in a non-normal distribution, and then the characteristics of the distribution are determined at 808. In one example, all calculated lambda differentials may be plotted together, and a distribution curve may be drawn based on the plotted data. In another example, N data sets may be generated from the calculated differentials, and the extreme values from each data set of lambda differentials may be determined. For example, 100 data sets may be generated, and the highest and/or lowest value from each data set may be chosen as the extreme values. These extreme values may be plotted and a distribution curve determined. In one embodiment, determining a distribution curve based on extreme values may include a generalized extreme value (GEV) distribution:

$$f(x)\Big|_{k,\sigma,\mu} = \frac{1}{\sigma}\left[1 + k\left(\frac{x-\mu}{\sigma}\right)\right]^{(-1/k)-1} e^{\left\{-\left[1-k\left(\frac{x-\mu}{\sigma}\right)\right]^{-1/k}\right\}}$$

Where k is the shape, σ is the scale, and μ is the location of the distribution curve.

In one embodiment, the characteristics of the distribution may include the magnitude of a central peak and of a mode of the distribution. The mode is the value that occurs most frequently in the distribution, and the central peak is the percentage of the data samples that have that value. In a GEV distribution, the mode may be determined by the equation:

$$\mathrm{Mode}[x] = \mu + \frac{\sigma}{k}\left[(1+k)^{-k} - 1\right]$$

A sensor degradation behavior may be determined based on the characteristics of the distribution at 810. For example, as will be explained in more detail below, the magnitude of the central peak (which indicates the degree of variation of the extreme lambda differentials) may indicate whether or not an asymmetric delay degradation behavior is present, as sensors with asymmetric delay type degradation may exhibit less variation than sensors without asymmetric delay. Additionally, the magnitude of the mode (which indicates whether the sensor output is biased rich or lean) may indicate whether or not an asymmetrical response degradation behavior is present. By determining the magnitude of the central peak and the magnitude of the mode, as well as determining other sensor parameters as will be described in more detail below, the sensor can be classified into one or more of the six discrete degradation behaviors, or be classified as not degraded. Determining the sensor degradation behavior based on the characteristics of the distribution will be described in more detail with regard to FIG. 9.

At 812, method 800 comprises determining if sensor degradation is indicated. If no degradation is indicated (e.g., the characteristics of the distribution indicate that no degradation behavior is present), method 800 returns to continue to monitor the sensor. If degradation is indicated, method 800 proceeds to 814 to determine the whether the sensor degradation behavior exceeds a maximum value. As described above, sensor degradation may be indicated based on the characteristics of an extreme value distribution of lambda differentials. The characteristic that indicates degradation (e.g., the central peak or mode) may be analyzed to determine the extent of the degradation. For example, a central peak magnitude above a given first threshold may indicate an asymmetric delay degradation behavior. If the magnitude is above the first threshold by a sufficient amount, for example if it is 20% or more greater than the first threshold, the degradation behavior may exceed the maximum limit. If the degradation behavior exceeds the maximum value, this may indicate the sensor is damaged or otherwise non-functional and as such method 800 proceeds to 816 to notify an operator of the vehicle of the sensor degradation, for example by activating a malfunction indication light. If the degradation behavior does not exceed the maximum value, it may indicate that the sensor is still functional. However, to ensure adequate engine control to maintain engine emissions and fuel economy at a desired level, one or more engine operating parameters may be adjusted at 818, if desired. This may include adjusting fuel injection amount and/or timing, and may include adjusting control routines that are based on feedback from the degraded sensor to compensate for the identified degradation.

Figure 11A:
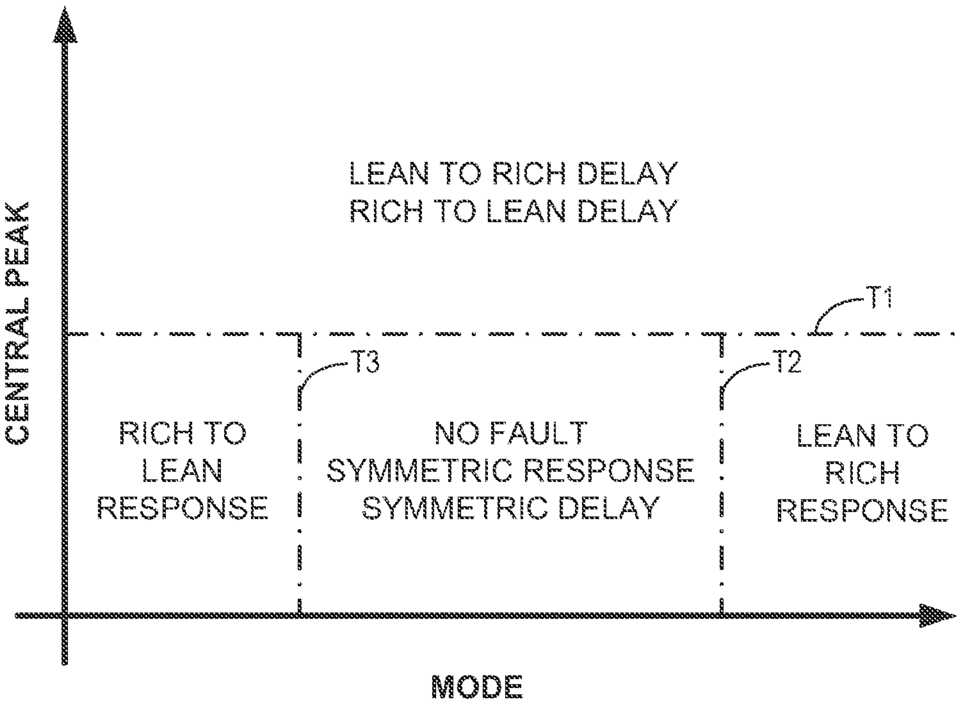
FIGS. 11A and 11B show an example diagrams illustrating seven exhaust gas sensor classifications based on model parameters according to an embodiment of the present disclosure.
Figure 11B:
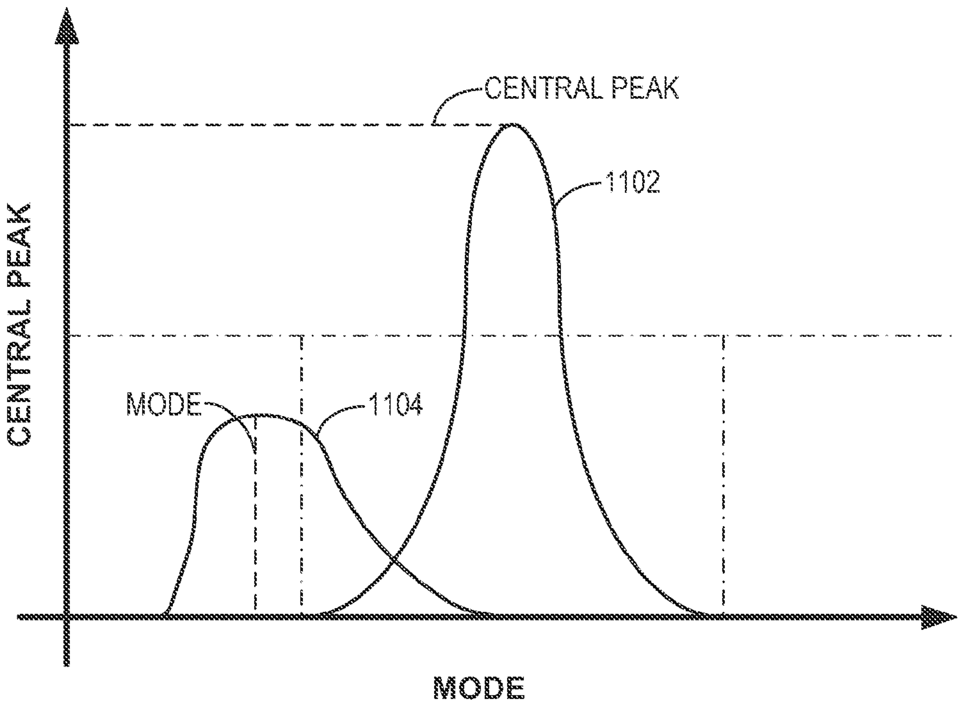

As explained above, method 800, as well as method 900 described with respect to FIG. 9 below, indicate sensor degradation based on characteristics of a distribution of extreme values of calculated lambda differentials collected during engine operation. These characteristics are illustrated in the example graphs of FIGS. 11A and 11B. FIG. 11A shows four distinct regions of an example graph where an extreme value distribution may be mapped. On the y-axis is the probability function of the distribution (the central peak), or the percentage of the samples for each value on the x-axis. On the x-axis is the calculated lambda differentials (the mode). As explained below, the sensor degradation may be determined based on the magnitude of the central peak and the mode. FIG. 11B shows an example graph illustrating two example extreme value distribution curves, 1102 and 1104.

Turning to FIG. 9, a method 900 for determining sensor degradation behavior based on the characteristics of the extreme value distribution is depicted. Method 900 may be carried out as part of method 800, for example at 810 of method 800. Method 900 includes, at 902, determining if the central peak of the distribution is less than a first threshold. As explained above with respect to FIG. 8, the central peak is the percentage of the data samples that have the most common value. Because the distribution is based on lambda differentials, a relatively high amount of variation is expected in the distribution when the exhaust gas sensor is functioning normally. Thus, a lack of variation, which results in a high central peak, indicates sensor degradation. Specifically, a high central peak indicates an asymmetric delay behavior, wherein the time delay from when a commanded change in air/fuel ratio is received to when the change actually occurs is larger than expected. Because the delay is asymmetric, either more time will be spent at rich operation (if the delay is a rich-to-lean delay) or more time will be spent at lean operation (if the delay is a lean-to-rich delay). In either case, less overall variation will be present. The first threshold may be determined in a suitable manner. In one embodiment, the distribution of the extreme values may be determined off-line for a new, non-degraded sensor, and the first threshold may be the central peak of the distribution of the non-degraded sensor. Further, the first threshold may be adjusted to either increase or decrease the sensitivity of the degradation detection. An example first threshold, T1, is illustrated in FIG. 11A.

If the central peak is not less the first threshold, an asymmetric delay sensor degradation behavior is indicated. An example GEV distribution with a central peak greater than the first threshold is illustrated as curve 1102 of FIG. 11B. Method 900 proceeds to 904 to determine if an expected lambda is greater than a determined lambda at idle, in order to determine which asymmetric degradation behavior is present. If the central peak is greater than the first threshold, the controller may determine a mean lambda for a given duration during a subsequent idle operation. If the determined mean lambda value is less than the expected or commanded mean lambda value, this indicates more time is spent in rich operation than commanded, and as such method 900 includes indicating a rich-to-lean delay sensor degradation behavior at 906. If the determined mean lambda value is greater than the expected value, this indicates more time is spent in lean operation, and method 900 includes indicating a lean-to-rich delay sensor degradation behavior at 908.

Returning to 902, if the central peak is less than the first threshold, method 900 proceeds to 910 to determine if the mode of the distribution is less than a second threshold. As explained above, the mode is the lambda differential value that occurs in the distribution most frequently. A symmetric sensor, that is a sensor that does not display any asymmetric sensor degradation, will typically have a mode in a symmetric range centered around zero, bounded by a second and third threshold. The second and third thresholds can be determined in a manner similar to the first, central peak threshold. Example second and third thresholds, T2 and T3, are illustrated in FIG. 11A.

If the mode is smaller or larger than the symmetric range, asymmetric response type degradation behavior is indicated. If the mode is larger than the symmetric range, that is if the mode is not less than the second threshold, method 900 proceeds to 912 to indicate a rich-to-lean response degradation. In this case, the sensor experiences a delay in the response to a commanded rich to lean change, and thus spends less time at the commanded lean lambda, than at the commanded rich lambda. Thus, a greater amount of the lambda differentials will occur with values with a positive (lean) magnitude.

If the mode is less than the second threshold, method 900 proceeds to 914 to determine if the mode is greater than the third threshold. If not, the mode is therefore less than the symmetric range, and thus method 900 includes indicating a lean to rich response degradation at 916. An example GEV distribution curve with a mode less than the third threshold is illustrated as curve 1104 of FIG. 11B. If the mode is greater than the third threshold, the mode is in the symmetric range. Based on the characteristics of the distribution, symmetric delay and response degradation as well as no degradation cannot be distinguished from each other.

To determine which symmetric condition the sensor is exhibiting, method 900 includes determining if the sensor time delay is less than or equal to a nominal time delay at 918. The nominal sensor time delay is the expected delay in sensor response to a commanded air/fuel ratio change based on the delay from when the fuel is injected, combusted, and the exhaust travels from the combustion chamber to the exhaust sensor. The determined time delay may be when the sensor actually outputs a signal indicating the changed air/fuel ratio. If the time delay is not less than or equal to the nominal time delay, method 900 proceeds to 920 to indicate a symmetric delay.

If the time delay is less than or equal to the nominal time delay, method 900 proceeds to 922 to determine if a time constant of the sensor is less than or equal to a nominal time constant. The nominal time constant may be the time constant indicating how quickly the sensor responds to a commanded change in lambda, and may be determined off-line based on non-degraded sensor function. If the determined time constant is greater than the nominal time constant, it indicates a slow response rate, and thus at 924, if the time constant is not less than or equal to the nominal time constant, a symmetric response degradation behavior is indicated.

If the time constant is less than or equal to the nominal time constant, method 900 includes indicating no degradation at 926. No degradation is indicated due to the characteristics of the distribution indicating a symmetric behavior of the sensor, and both the sensor time constant and delay being similar to the nominal time constant and delay. Upon indicating a sensor behavior, whether one of the six discrete degradation behaviors or the no degradation behavior, method 900 exits.

Thus, the methods described with respect to FIGS. 8 and 9 provide for monitoring an exhaust gas sensor, in order to determine a sensor degradation behavior. If sensor degradation is determined, the severity of the degradation may be evaluated. If the degradation is severe, replacement/repair of the sensor may be indicated to an operator of the vehicle. If the degradation is less severe, the current sensor may continue to be operated. However, the control routines involving the sensor may be adapted based on the degradation. For example, the time constant and/or delay constant of the sensor used in feedback control of the air/fuel ratio may be adjusted. Further, as fuel injection timing and amount is determined based on feedback from downstream exhaust gas sensors, the amount and/or timing of the fuel injected may be adjusted to maintain engine control and vehicle emissions in a desired range.

While the methods described with respect to FIGS. 8 and 9 classify sensor function into one of seven classes, in some embodiments, the sensor may exhibit more than one class of sensor degradation. For example, if the central peak of the GEV distribution is near the first threshold and the mode of the distribution is greater than the symmetric range, both a lean to rich response and a lean to rich delay may be indicated. Further, the method of FIGS. 8 and 9 non-intrusively monitor the exhaust gas sensor by collecting data during steady state operating conditions. However, in some embodiments, the engine may purposely be commanded to operate rich or lean while executing the methods. This type of operation may be used to validate the determination of the sensor degradation based on the characteristics of the distribution as described.

Figure 10:
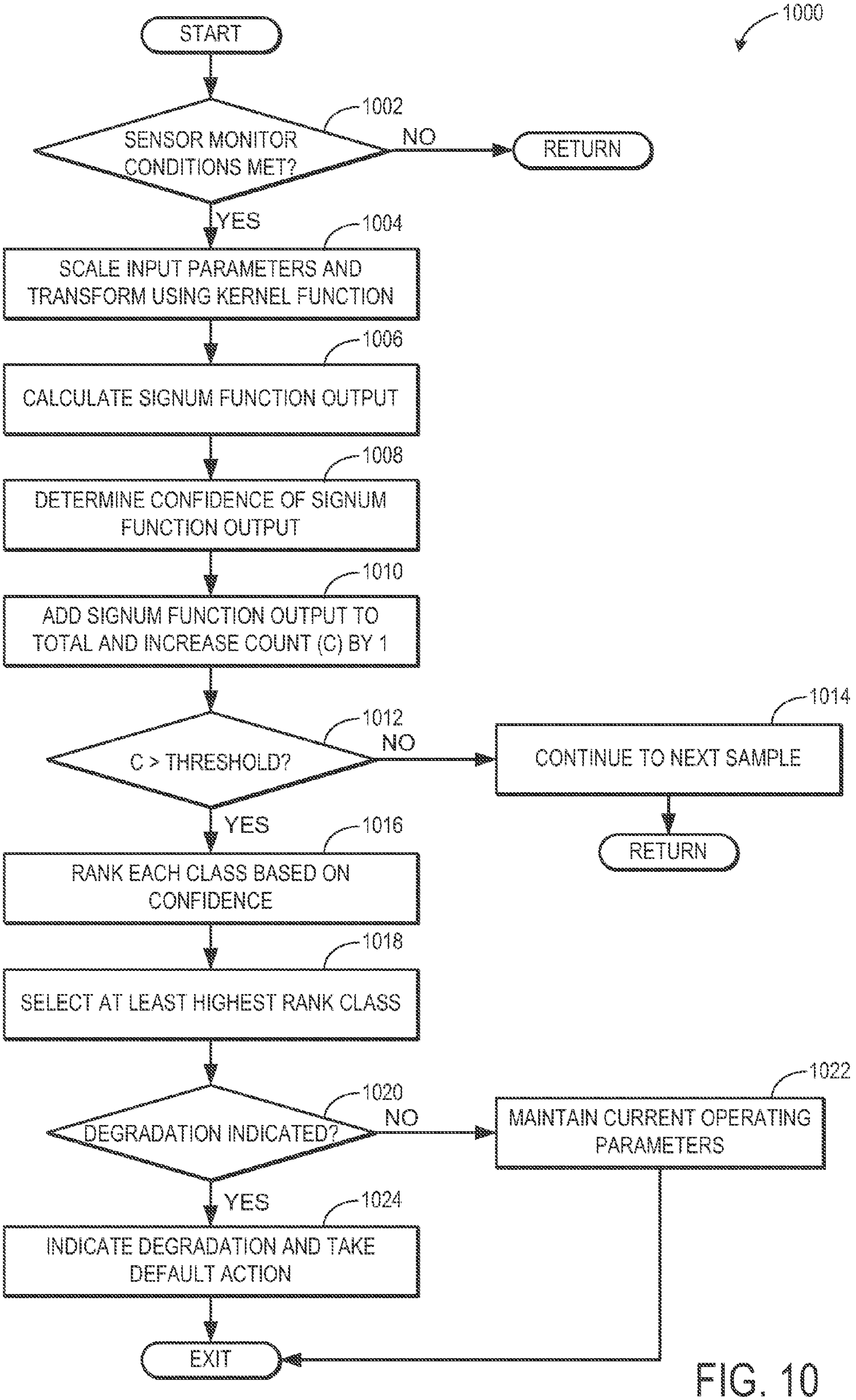
FIG. 10 shows a flow chart illustrating a method for determining exhaust gas sensor degradation behavior according to another embodiment of the present disclosure.

Turning to FIG. 10, another embodiment for non-intrusive monitoring of exhaust gas sensor functioning is depicted. In this embodiment, a support vector machine (SVM) may be used by a sensor monitor to predict sensor degradation behavior. The SVM may be trained using pre-classified, known input parameters. During operation of a vehicle under selected conditions, various unclassified input parameters may be fed into the trained SVM model, and after a predefined number of samples have been classified, the total of each classification may be compared to a threshold to determine whether or not the sensor is operating with one of the six fault conditions.

SVM is a supervised learning algorithm, where given a training set with known class information, a model is developed to classify the unknown test samples into different classes. The SVM processes a set of input data and predicts, for each given input, which of two possible classes the input is a member of, which makes the SVM a non-probabilistic binary linear classifier. In one embodiment, the SVM predicts whether or not the exhaust gas sensor is operating with one of the six sensor degradation behaviors. Typically, the SVM algorithm may be generated via a plurality of sets of training examples, each marked as belonging to one of two categories. The SVM training algorithm builds a model that assigns new examples into one category or the other. However, to differentiate among multiple classes, the SVM algorithm may be trained with multiple training sets, where each set is marked as belonging to one of the six classes of sensor degradation, or not belonging to that class.

An SVM model is a representation of the examples as points in space, mapped so that the examples of the separate categories are divided by a clear gap (sometimes referred to as a margin) that is as wide as possible. New examples are then mapped into that same space and predicted to belong to a category based on which side of the gap they fall on.

In the depicted embodiment, the SVM may classify unknown inputs into one of seven classes, the six sensor degradation behaviors described with respect to FIGS. 2-7, or a no degradation condition. As such, the SVM algorithm may include an any-of multi-classifier, a one-of multi-classifier, or other suitable method for determining which of the seven classes the exhaust gas sensor is in, as described in more detail below.

SVMs use a signum function as a linear classifier to classify the unknown inputs into the two groups based on the training function wherein known inputs are used. Specifically, the known inputs are mapped onto high- or infinite-dimensional space and one or more hyper-planes are chosen that separate the inputs into the two spaced groups. In some embodiments, a hyper-plane that represents the largest margin of separation of the groups is chosen, while in other embodiments, a hyper-plane with a margin that allows for some degree of error in the inputs may be chosen, known as a slack margin. After the model is trained, unknown inputs can be entered and classified into one of the two groups. Typically, the output of the signum function is either +1 or −1, but either classification may be transformed into other values, e.g., −1 may be transformed to 0.

If the known inputs used to train the model cannot be separated using a linear classification, a transformation function may be used with a non-linear classification to separate the inputs. Example transformation functions include radial basis functions, linear transformations, etc. Additionally or alternatively, soft margins may be used to introduce some slack variables to the classification to allow some misclassification for outlier data points.

For sensor diagnostics, various input parameters into the SVM may be used. In one embodiment, the input parameters may include air amount (AM) such as mass airflow rate from MAF sensor, sensor temperature estimated based on engine operating conditions such as speed, load, etc., upstream exhaust gas sensor output (e.g., UEGO output), and downstream exhaust gas sensor output (e.g., HEGO output). In some embodiments, all the example inputs listed above may be used in the SVM. In other embodiments, only a subset of the input parameters may be used, such as sensor temperature and output.

FIG. 10 is a flow chart illustrating a method 1000 that may be executed by controller 12 and/or controller 140 in order to monitor sensor function. In this example, the inputs are each selected from the same sample instance (e.g., sample time) and provided to the SVM algorithm to generate a classification output. As will be described in more detail below, a plurality of classifications are generated for a plurality of respective sample instances over a duration of engine operation following the engine start. Once a classification is generated over the entire duration, a percentage of acceptable performance classifications out of the total number of classifications made during the duration is compared to a threshold to determine whether the exhaust gas sensor exhibits a degradation behavior. If not, the process is repeated for a plurality of durations until repeatable results are obtained for identifying a sensor degradation behavior.

Because there are seven possible sensor degradation behaviors (the six discrete degradation behaviors and no degradation), a multiple classification scheme is used to differentiate among the degradation behaviors. As will be described below, each input may be fed into the SVM algorithm seven times, and marked as belonging or not belonging to each of the seven degradation behaviors. Then each classification may be given a confidence level based on how close that input value is to the support vectors (e.g., the values that define the margin). For example, inputs that are further away from the support vectors may be given higher confidence levels. After all the samples in a duration have been classified for all the degradation behaviors, the behaviors may be ranked based on the confidence levels.

Method 1000 comprises determining at 1002 if the engine is running and if selected conditions are met. The selected conditions may include that the input parameters are operational, for example, that the UEGO and HEGO sensors are at a temperature whereby they are outputting functional readings. Further, the selected conditions may include that combustion is occurring in the cylinders of the engine, e.g. that the engine is not in a shut-down mode such as deceleration fuel shut-off (DFSO), or that the engine is operating in steady state conditions.

If it is determined that the engine is not running and/or the selected conditions are not met, method 1000 returns and does not monitor sensor function. If the engine is running and the selected conditions are met, method 1000 proceeds to 1004 to scale the input parameters and transform using a kernel function. As explained above, non-linear inputs may be transformed using the kernel function. Various kernel functions may be used, such as a linear, polynomial, radial basis function, sigmoid, and others. In one example, the radial basis function may be used:

$$K(x_i,x_j)=\exp(-\gamma\|x_i-x_j\|^2)$$

In one embodiment, γ=600, and the soft basis parameter C=650, where $x_i$, $x_j$, . . . etc. are the input parameters (e.g., MAF, temperature, sensor output).

At 1006, the signum function output is calculated for each of the seven degradation behaviors. The signum function determines a sign, or classification, for the output of the SVM. The SMV may be trained based on known inputs, and may include a set of model parameters that are used to predict an output from unclassified input parameters. Each input parameter determined at a single instance of time may be fed into the SVM model, and a signum function output produced based on:

$$y_i=+1 \text{ if } (\langle w,x_i \rangle + b) \geq 1$$

$$y_i=-1 \text{ if } (\langle w,x_i \rangle + b) \leq 1$$

With a hyper-plane of $\langle w,x_i \rangle$ +b=0, and where $y_i$ is the predicted class for the test input $x_i$. w is defined by the trained SVM model based on the support vectors computed from optimizing the margin of the hyper-plane.

In one embodiment, to reduce the number of support vectors or to reduce the data size of the trained model for implementation in a vehicle, clustering can be used. Clustering includes an un-supervised learning where the data set is divided into different clusters or groups, so as to minimize the total distance of each point from the respective centroid. In a simpler language, the datapoints which are closer to each other are assigned to one cluster. This technique is employed to initially divide the training set into K (pre-defined number) clusters in each class and then the SVM algorithm is used where the original dataset is replaced by the centroids of each cluster. It was observed that the significant reduction in the number of support vectors could be achieved without loss in accuracy.

At 1008, the output of the signum function is given a confidence level. In one example, this may include determining the difference between the input value and the nearest support vector. A running total of the confidence levels for each output of each class of sensor degradation may be stored.

At 1010, the output of the signum function is added to the total of all previously calculated outputs and the count (C) is increased by 1. In doing so, over a given duration (j), which may start following an engine start and once the input parameters can be reliably sensed the method determines for each sample instance (i) a classification CL based on the calibrated and trained support vector machine.

$$\left.\begin{matrix} x1_i \\ x2_i \\ x3_i \\ x4_i \\ x5_i \end{matrix}\right\} \rightarrow SVM(x1_i x2_i x3_i x4_i x5_i) \rightarrow CL_i$$

Where CL is the output of the signum function, and is either set to 1 or −1, but with −1 converted to zero. Then, the routine adds $CL_i$ to the running count $C_j$:

$$C_j=C_{j-1}+C_j$$

The count (C) is compared to a first threshold at 1012, and if C is above the threshold (e.g., the duration is complete) method 1000 proceeds to 1016. If C is not above the threshold, method 1000 proceeds to 1014 to continue to the next sample.

At 1016, each degradation class is ranked based on the associated confidence levels determined at 1008, as well as other parameters, such as the frequency/distribution of classifications within the classes. At 1018, the at least highest ranked class is selected. The highest ranked class may be the degradation behavior that the sensor is most likely to be exhibiting. In some embodiments, more than one sensor degradation behavior may be present. In such cases, the top two classes may selected. The determination which top-ranked classes to select may be determined in a suitable manner dependent upon the stringency of the degradation determination.

At 1020, it is determined if sensor degradation is indicated (e.g., if a class other than no degradation is selected at 1018). If not, method 1000 proceeds to 1022 to maintain current operating parameters. If degradation is indicated, method 1000 proceeds to 1024 to indicate sensor degradation and take default action. The indication may include notification being sent to a driver via a message system, or may be the setting of a diagnostic code read by a diagnostic code reader in a service station, or various other indications such as a malfunction indicator lamp (MIL).

The duration (j) may a suitable duration. For example, in one embodiment, the duration may include idle operation, or operation under steady state conditions. The duration may be long enough to collect a suitable number of inputs in order to reliably test the sensor function, e.g., 10 seconds, 60 seconds, etc. Further, more than one duration of samples may be collected during operation of the sensor monitor. The plurality of durations may include combinations of the above durations. In some embodiments, the plurality of durations may occur successively, that is, without an engine shutdown occurring between them.

The indication of degradation is as determined by method 1000 may be based on the parameter readings occurring during the indicated duration. For example, the indication of degradation may be based on parameter readings occurring during idle operation as explained above. Further, the indication of degradation may be based on parameter readings occurring engine temperature is above light-off temperature, or may be based on parameter readings occurring when engine speed is constant, etc.

While the method described above with respect to FIG. 10 determines sensor degradation by classifying each input parameter seven times and ranking the resultant output, other suitable mechanisms may be used. For example, one SVM classification for each input may be performed using an area of space that includes multiple hyper-planes. The multiple hyper-planes may be determined such that seven regions in space exist corresponding to the seven sensor behaviors, and each input is classified into one of the seven regions.

Thus, the method of FIG. 10 provides for monitoring an exhaust gas sensor. In one example, a method includes applying a set of inputs for a given sample to a support vector machine to generate a classification output, recording a plurality of classification outputs for a plurality of successive samples over a duration, ranking each of the plurality of classifications based on confidence levels associated with each classification output, and indicating a sensor condition based on at least the highest ranked classification.

It will be appreciated that the configurations and methods disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of monitoring an exhaust gas sensor coupled in an engine exhaust, comprising:
collecting a plurality of sets of lambda differentials during selected engine operating conditions from an exhaust sensor;
indicating exhaust gas sensor degradation based on characteristics of a distribution of extreme values of the plurality of sets; and
adjusting a fuel injection amount and/or timing based on the indicated degradation.

2. The method of claim 1, wherein the distribution is a generalized extreme value (GEV) distribution, and wherein the characteristics include a magnitude of a mode and of a central peak of the GEV distribution.

3. The method of claim 2, wherein if the magnitude of the central peak is greater than a threshold, indicating an asymmetric delay sensor degradation.

4. The method of claim 3, wherein if an expected mean air/fuel ratio is greater than a determined mean air/fuel ratio at idle, indicating a rich to lean delay sensor degradation, and if the expected mean air/fuel ratio is less than the determined mean air/fuel ratio at idle, indicating a lean to rich delay sensor degradation.

5. The method of claim 3, wherein if the magnitude of the central peak is less than the threshold and the magnitude of the mode is outside a symmetric range, indicating an asymmetric response sensor degradation.

6. The method of claim 5, wherein if the magnitude of the mode is less than the symmetric range, indicating a lean to rich response sensor degradation, and if the magnitude of the mode is greater than the symmetric range, indicating a rich to lean response sensor degradation.

7. The method of claim 5, wherein if the magnitude of the mode is in the symmetric range, indicating no degradation or a symmetric sensor degradation.

8. The method of claim 7, further comprising indicating a symmetric delay sensor degradation if a determined time delay is greater than a nominal time delay, and indicating a symmetric response sensor degradation if a determined time constant is greater than a nominal time.

9. The method of claim 1, wherein the selected engine operating conditions further comprise steady state operating conditions.

10. A system for a vehicle, comprising:
an engine including a fuel injection system;
an exhaust gas sensor coupled in an exhaust system of the engine; and
a controller including instructions executable to:
indicate exhaust gas sensor degradation based on characteristics of a distribution of extreme values of a plurality of sets of lambda differentials collected during steady state operating conditions; and
adjust an amount and/or timing of fuel injection based on the indicated sensor degradation.

11. The system of claim 10, wherein the instructions are further executable to notify an operator of the vehicle if the indicated sensor degradation exceeds a threshold.

12. The system of claim 10, wherein the distribution is a generalized extreme value (GEV) distribution, and wherein the characteristics include a magnitude of a mode and of a central peak of the GEV distribution.

13. A method of monitoring an oxygen sensor coupled in an engine exhaust, comprising:
collecting a plurality of sets of lambda differentials from an exhaust sensor;
indicating an asymmetric delay sensor degradation if a first characteristic of a distribution of extreme values of the plurality of sets exceeds a first threshold;
indicating an asymmetric response sensor degradation if the first characteristic is below the first threshold and a second characteristic of the distribution is outside a second threshold range; and
adjusting a fuel injection amount based on an indicated sensor degradation.

14. The method of claim 13, wherein the first characteristic a magnitude of a central peak of the distribution and the second characteristic is a magnitude of a mode of the distribution.

15. The method of claim 13, further comprising indicating a no fault or symmetric sensor degradation if the first characteristic is below the first threshold and the second characteristic is within the second threshold range.

16. The method of claim 15, further comprising indicating a symmetric delay sensor degradation if a determined time delay of the sensor is greater than a nominal time delay, and indicating a symmetric response sensor degradation if a determined time constant of the sensor is greater than a nominal time constant.

17. The method of claim 13, wherein the lambda differentials are collected during steady state operating conditions.

18. A method of monitoring an exhaust gas sensor, comprising:
successively sampling the exhaust gas sensor over a duration;
applying a set of inputs for a given sample to a support vector machine to generate a classification output;
recording a plurality of classification outputs for the successive samples;
ranking each of the plurality of classification outputs based on confidence levels associated with each classification output;
indicating a sensor condition based on at least a highest ranked classification output; and
adjusting a fuel injection amount and/or timing based on the indicated sensor condition.

* * * * *